United States Patent [19]

Butler

[11] Patent Number: 4,645,536
[45] Date of Patent: Feb. 24, 1987

[54] PROCESSES FOR EXTRACTING FUNGI-TOXIC MATERIAL FROM WOOD MATERIAL OF A DECAY RESISTANT SPECIES

[75] Inventor: Robert A. Butler, New Brunswick, Canada

[73] Assignee: County Wood Products Ltd., New Brunswick, Canada

[21] Appl. No.: 771,408

[22] Filed: Aug. 30, 1985

[51] Int. Cl.$^4$ .......................... B05D 1/18; C09D 5/14
[52] U.S. Cl. .................... 106/15.05; 427/440; 428/541; 428/907
[58] Field of Search ............. 427/325, 440, 441; 428/907, 541; 106/15.05

[56] References Cited

U.S. PATENT DOCUMENTS 4,413,023  11/1983  Chow ........................ 427/440 X

FOREIGN PATENT DOCUMENTS 629760  10/1961  Canada .
979754  12/1975  Canada .

OTHER PUBLICATIONS

*The Chemistry and Utilization of Western Red Cedar*, G. M. Barton and B. F. MacDonald, Dept. of Fisheries and Forestry, Can. Forestry Service Publication No. 1012 (1971).
*Extractivities of Eastern White Cedar Heartwood*, N. Levitim and G. Besserer, Dept. of Forestry Project #0-186-10, Oct. 1985.
*The Cause of Natural Durability in Timber*, P. Rudman, Holzforschung, 16(3) 1962, pp. 74–77.
*Antiobiotic Substances from the Heart Wood of Thuja Plicata D. Don*, Jarl Gripenberg, Acta Chemica Scandinavia, 2(1984), 639–643.
*Toxicity Tests of a New Tropolone, β-Thujaplicinol Occurring in Western Red Cedar*, J. W. Roff and E. I. Whittaker, Canadian Journal of Botany, vol. 37, (1959) 1132–1133.
*The Chemical Nature of the Acetone Extractive of Western Red Cedar*, G. M. Barton and J. A. F. Gardner, Pulp and Paper Magazine of Canada, 55(10)1954.
*Analytical Method for Thujaplicin*, J. MacLean and J. Gardner, 1956, Acta Chemica Scandinavia, 28:589–512.
*Distribution of Fugicidal Extractives in Western Red Cedar Heartwood*, H. MacLean and J. Gardner, Forest Products Journal, Dec. 1956, 510–516.
*Pulp and Chemical Potential for Western Red Cedar Utilization*, J. D. Wethern, Forest Products Journal, Sep. 1959.
*Toxicity Tests of Water–Soluble Phenolic Fraction of Western Red Cedar*, J. W. Roff and J. M. Atkinson, Canadian Journal of Botany, vol. 32 (1954).
*Weathering Effect on Thujaplicin Concentration in Western Red Cedar Shakes*, Eric Johnson & A. J. Cserjesi, Forest Products Journal, vol. 30, No. 6, pp. 52–53.
*Utilizing Residue From Western Red Cedar Mills*, C. F. McBride Forest Products Journal, Sep. 1959, pp. 313–316.
*Antibacterial Activity of β–Thujaplicin*, T. J. Trust and R. W. Coombs, Canadian Journal of Microbiology, 1973, 19, 11, pp. 1341–1346+1 PL.

*Primary Examiner*—Michael R. Lusignan
*Attorney, Agent, or Firm*—Watson, Cole, Grindle & Watson

[57] ABSTRACT

Disclosed is process for extracting fungi-toxic material from wood material of a species of wood which is resistant to fungi-growth. The process comprises providing a first quantity of the wood material, contacting said quantity with an extraction agent in an amount and for a time sufficient to extract essentially all fungi-toxic material in the wood material, separating the agent containing the fungi-toxic material from the wood material, contacting a second quantity of wood material with the separated extraction agent for a time sufficient to extract fungi-toxic material contained in the second quantity of wood material, and separating the extraction agent from the second quantity of wood material.

11 Claims, 2 Drawing Figures

PROCESSES FOR EXTRACTING FUNGI-TOXIC MATERIAL FROM WOOD MATERIAL OF A DECAY RESISTANT SPECIES

The present invention relates to processes for extracting fungi-toxic materials from stain and decay resistant species of wood such as eastern white cedar and, more particularly, to processes for extracting such fungi-toxic materials which yield solutions which are rich in the fungi-toxic materials that can be used to treat wood materials susceptible to fungi damage to provide long term fungi resistence, e.g., up to ten years or more. The invention further relates to processes for treating decay and stain susceptible wood materials with the aforementioned fungi-toxic material rich solutions to impart stain and decay resistance to the wood materials.

BACKGROUND OF THE INVENTION

Many species of commonly used wood such as pine, hemlock and the like have relatively poor resistance to stain and decay caused by various forms of common fungi. Thus untreated products, e.g., non-kiln dried products, such as lumber, poles, posts and like made from these woods may have a limited useful life when stored or utilized in a moist environment where contact with fungi can be expected. For example, the growth of fungus on wet raw wood material of a fungi susceptible species oftentimes occurs within two or three weeks after initial exposure to a warm, moist environment. Fungal growth typically manifests itself initially as an objectionable stain on the surface of the wood material and such growth can, over an extended period of time, cause decay and destruction of the wood material.

It has been a fairly common practice in the lumber industry to treat such fungi susceptible wood products with various chemical agents to impart fungi-induced stain and rot resistance to the products. The most widely used agents in recent years have included chlorophenols such as pentachlorophenol and copper chromium arsenates. While these agents in most instances provide sufficient protection for the treated wood products, adverse health and environmental risks are posed by the use of these chemicals.

It has been recognized for some time that certain species of wood such as various species of cedar wood are significantly more resistant to stain and decay caused by fungi then other species of wood. This characteristic of these species of wood has been attributed to their relatively high content of $\alpha$, $\gamma$, and B-thujaplicin, B-dolabrin, B-thujaplicinol, thujic acid and methyl thujate, the thujaplicins being the primary constituent and are recognized as the primary agents responsible for decay resistance. The sum total of these chemicals may be quantified as "thujaplicin equivalents".

U.S. Pat. No. 4,413,023 to Chow, issued on Nov. 1, 1983, discloses a method of treating wood to prevent stain and decay which includes extracting from a decay resistant species of wood material fungi growth inhibiting material and wetting the surface of wood to be treated with a solution of the extracted material. It is further taught in this patent that the extraction of the fungi growth inhibiting material from the decay resistant species of wood material is accomplished by immersing the wood material in an extracting solvent for a period of time ranging from four to twenty-four hours and then decanting the solution for use in treating wood material. A significant drawback of this extraction is that the solutions obtained are relatively weak in concentration of the fungi growth inhibiting material and thus wood material treated with the solutions may be protected from fungal growth for a limited time period, generally less than about one year, sometimes six months or less.

SUMMARY OF THE INVENTION

It is therefore a feature of the present invention to provide processes for the extraction of fungi-toxic materials from decay resistant species of wood material with an extraction agent which yield a solution rich in the fungi-toxic materials, probably at or about the maximum concentation of the fungi-toxic material in the extraction agent.

It is another feature of the present invention to provide a process for treating products containing wood material of the type suceptible to damage by fungi such that the wood material tends not to be damaged by fungi for extended periods of time, generally up to ten years or more.

Briefly, the present invention in its broader aspects comprehends a process for extracting fungi-toxic material from wood material of a species of wood which is resistant to fungi-growth comprising providing a first quantity of the wood material, contacting said quantity with a fluid agent capable of extracting fungi-toxic material from the wood material, the agent being in an amount sufficient and in contact for a time sufficient to extract essentially ALL of the fungi-toxic material in the wood material, separating the agent containing the fungi-toxic material from the wood material, contacting additional wood material of a second quantity with the separated extraction agent for a time sufficient to extract fungi-toxic material in the second quantity of wood material, and separating the extraction agent from the second quantity of wood material.

Further objects, advantages and features of the present invention will become more fully apparent from a detailed consideration of the arrangement and construction of the constitutent parts as set forth in the followng description taken together with the accompanying drawing.

DETAILED DESCRIPTION OF THE PREFERRED EMBODIMENTS

As was mentioned previously, the present invention relates to processes for extracting fungi-toxic materials from decay resistant species of wood material. The processes of the present invention are predicated on the realization that extractions of a given quantity of wood material by a volume of extraction agent sufficient to extract substantially all of the fungi-toxic material yields a concentration of fungi-toxic material in the agent which is well below the maximum possible concentration of the material. For example, it has been determined that the maximum concentration of B-thujaplicin equivalents extracted from eastern white cedar in aqueous solutions of borax is generally about 150 mg/l to 250 mg./l.

Thus, the processes of the invention basically involve contacting a quantity of wood material containing fungi-toxic materials with an extraction agent to effect transfer of the fungi-toxic materials to the agent as a solution, separating the solution from the spent residual wood material and then repeating the sequence on fresh quantities of wood material until the solution reaches near maximum concentration.

Among the various species of wood materials suitable in the subject processes, there may be mentioned western red cedar (Thuja plicata), yellow cedar (Chamaecyparis nootkatensis D. Don), eastern white cedar (Thuja Occidentalis), yew (taxus spp.), redwood (Sequoia spp.P) and teak (Tectona grandis L). A presently preferred wood material for use in the processes of the invention is eastern white cedar.

The wood material, for the obvious reason of economy, is preferably waste wood commonly the by-product of a lumber mill. In addition, the wood material, prior to extraction, is preferably in a relatively finely divided form such as chips, shavings, sawdust and like as extraction is enhanced by greater liquid-solid contact surfaces. If necessary, larger structures of wood material can be comminuted by methods such as by shredding and the like to provide an appropriately sized material.

Suitable agents for extacting fungi-toxic materials include a wide variety of aqueous and non-aqueous liquid media. Examples of suitable agents include water, aqueous solutions of borax, acetone, various alcohols and cholorform. The agent may be utilized at ambient temperature or at elevated temperatures. While chloroform is believed to be the most effective in extracting the fungi-toxic materials from the wood materials, its use on an industrial scale may be precluded for economic and environmental reasons. Consequently, aqueous borax solutions, e.g., of concentrations up to about 10% borax, are presently preferred due to their relatively high efficiency in extracting fungi-toxic materials, relatively low cost, and low environmental and occupational hazards.

Figure 1:
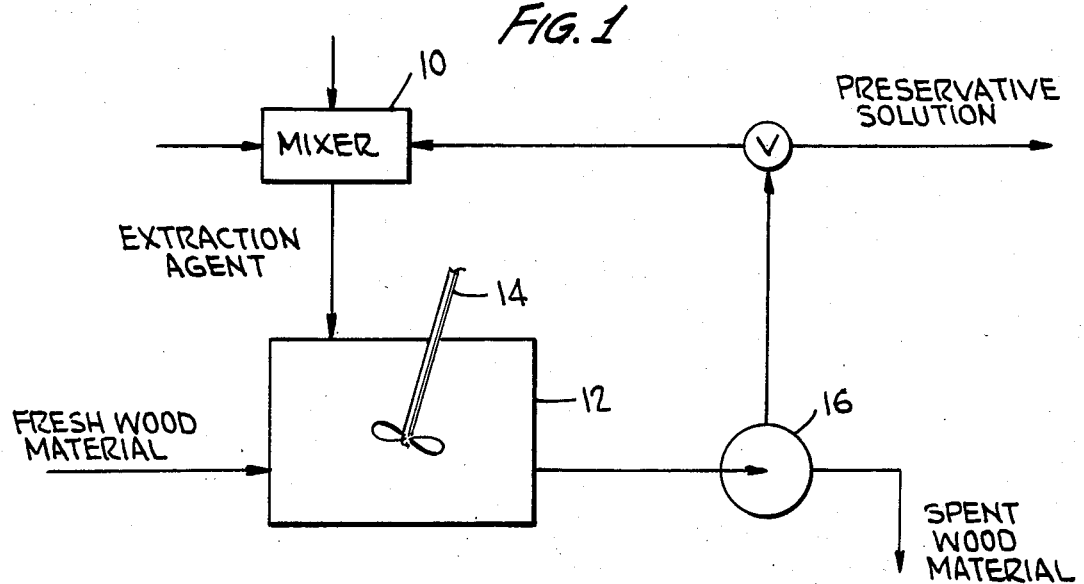
FIG. 1 is a schematic of one embodiment of a process according to the present invention.

The processes of the invention for extracting fungi-toxic materials from wood materials have the objective of optimizing the concentration of the fungi-toxic materials in the extraction agent. In one embodiment of the invention as illustrated in FIG. 1, the fungi-toxic materials are extracted in a recycle type batch process. As is shown, the extraction agent is prepared in mixer 10 and then transported to extraction tank 12 containing small pieces of wood material. Pereferably, tank 12 is agitated by stirrer 14 driven by any suitable means. After a suitable residence time in tank 12 such as about one hour, the substantial majority of fungi-toxic material has been extracted from the wood material into the extraction agent. The wood material-extraction agent slurry is withdrawn from extraction tank 12 and forwarded to filter 16.

In filter 16, the wood material is separated from the extraction agent containing fungi-toxic material and the wood material discarded. The extraction agent is then recycled back to mixer where optionally fresh make-up extraction agent is added to the recycled agent and the agent then forwarded to extraction tank 12 containing a new supply of wood material. The extraction and filtration procedure are conducted in the same manner as before and the procedure repeated until the agent contains at or near the maximized concentration of fungi-toxic material.

For example, in the extraction of eastern white cedar with a mild aqueous solution of borax, the concentration of fungi-toxic material maximizes around the fourth cycle with only a small concentration increase after three cycles. Thereafter, the extraction agent rich with fungi-toxic material is drawn-off for use as a stain and decay preservative for products of fungi-susceptible species of wood materials.

Figure 2:
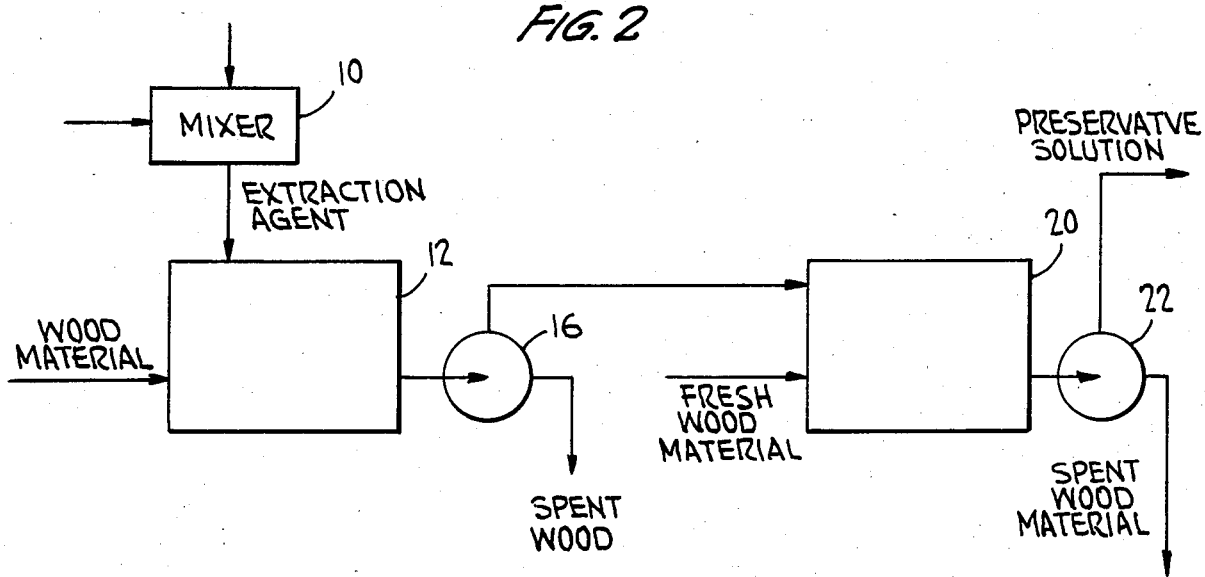
FIG. 2 is a schematic of another embodiment of a process according to the present invention.

FIG. 2 illustrates a variation on the process shown in FIG. 1. Like the previous described process, this process utilizes mixer 10 for formulating the extraction agent which is thereafter transported to extraction tank 12 containing fresh wood material. Tank 12 is of the non-agitated type. Extraction of the fungi-toxic material is conducted for a sufficient time period to extract essentially all of the fungi-toxic material from the wood material. The slurry of extraction agent and spent wood material is then passed to filter 16 where the two components are separated. Spent wood material is discarded from filter 16 and extraction agent enriched in fungi-toxic material is transported to second extraction tank 20 loaded with fresh wood material.

In extraction tank 20, extraction of additional fungi-toxic material is conducted in the same manner as in extraction 10 and thereafter the wood material is separated from the extraction agent in filter 22. The process is then repeated in additional extraction tanks and filters (not shown) until the extraction agent contains essentially the maximum amount of fungi-toxic material. Generally, for the extraction of eastern white cedar wood material with aqueous extraction agents, extraction in three or four successive tanks is sufficient to yield an extraction agent containing close or at the maximum concentration of fungi-toxic materials.

The extraction agent rich in fungi-toxic material produced by the processes disclosed herein is very useful in treating products containing wood of decay susceptible species to provide the product with resistance to decay, rot and staining caused by fungi. Generally, the products are treated by contacting the product with the extraction agent rich in fungi-toxic material by means such as dipping, brushing and spraying. A presently preferred process for treating wood containing products is by pressure impregnation to cause the extraction agent to deeply penetrate the wood surface. Wood products so treated by the extraction agents produced by the processes of the invention may be provided with resistence to attacks by fungi for periods of up to ten years or more.

The processes of the present invention are illustrated in the following examples. It should be understood that the examples are given for the purpose of illustration only and the examples do not limit the invention as has heretofore been described.

EXAMPLE I

A quantity of fresh waste wood from an eastern white cedar mill is shredded and is transferred into a large extraction tank similar to that shown in FIG. 1. Fresh water is mixed with borax to give a 2.0% aqueous borax solution and the solution is heated to approximately 20° C. The aqueous borax solution is then pumped into the extraction tank, the volume of liquid to weight of eastern white cedar waste wood being approximately 9 liters to 1 kg.

The slurry of eastern white cedar waste wood and the aqueous solution borax is then mechanically stirred for a period of about one hour to allow the maximum quantity of fungi-toxic materials to be extracted. The slurry of eastern white cedar waste wood and aqueous borax solution is then separated and the extracted eastern white cedar waste wood is then removed from the process and is further processed or disposed of.

The extracted solution of eastern white cedar waste wood after separation from the spent waste wood is then recycled into fresh eastern white cedar waste wood and the process repeated. After recycling a minimumn of three times and when the fungi-toxic chemical concentration measured as B-thujaplicin equivalents is about 150 mg/l, the solution is removed and stored as the end-product of the process.

EXAMPLE II

The fungi-toxic properties of the extracted solution of Example 1 were then compared against the properties of polychlorinated phenol and chromium copper arsenate by testing them against four wood destroying fungi selected on the basis of ASTM, method D 2017. Results from such tests indicated that the extract of eastern white cedar is approximately equivalent in fungal toxicity to polychlorinated phenol and more toxic than copper chromium arsenate.

The solution was then tested using the ASTM method for evaluating wood preservatives, specifically, ASTM method D1413. Pine blocks treated with eastern white cedar extract were all graded as being clear and free from decay after 16 weeks in an environment favorable for wood decay. The untreated control blocks showed as much as 45% loss in mass due to decay at 16 weeks.

EXAMPLE III

In this example, the amount of borax used in the extraction agent and the pH of the extraction agent were investigated.

A 0.5% borax solution was used to extract the thujaplicin containing fungi-toxic material from a quantity of eastern cedar mill waste wood in the manner of Example 1. This same extract solution was recycled seven times, each time contacted with fresh waste wood, with pH and thujaplicin equivalent content monitored at each recycle step. This procedure was replicated three times and then repeated using a 5% borax solution. The measured values indicated that the increment in thujaplicin equivalent concentration decreased with each recycle step, with the optimization cut-off being three recycle steps which resulted in B-thujaplicin equivalent concentrations of about 150 mg/l.

Of the several factors affecting the final concentration of thujaplicin equivalent in resultant solution, the most obvious would seem to be the saturation limit of B-thujaplicin equivalents in solution of around 150 mg/l and the pH of the solution. For the 0.5% borax solution, as the solution pH decreases, the extraction potential of the solution decreases and as the solution becomes pH neutral, the extraction potential becomes significantly smaller. However, the higher concentration of borax yielded results which were very similar to those of the low concentration which would indicate that pH is not the primary factor influencing the maximum extraction potential of the borax solution.

One method to estimate thujaplicin equivalent content is the colormetric method disclosed by H. MacLean and J. A. F. Gardner in an article entitled "Analytical Method for Thujapliciuns" in *Acta Chemica Scandinavia*, Vol. 28, No. 4 (1956).

The term "essentially all" as used herein in connection with the amount of fungi-toxic material extracted from a particular quantity of wood material may be defined as the amount of fungi-toxic material capable of being extracted by the particular extraction utilized, it being recognized that the various extraction agents may have different total extraction capabilities for the fungi-toxic material. In most instances, "essentially all" means in excess of about 90% of all fungi-toxic material contained in the wood material.

While there has been shown and described what is considered to be preferred embodiments of the present invention, it will be obvious to those skilled in the art that various changes and modifications may be made therein without departing from the invention as defined in the appended claims.

It is claimed:

1. A process for extracting fungi-toxic material from wood material of a species of wood which is resistant to fungi-growth, the process comprising providing a first quantity of the wood material, contacting said quantity with an extraction agent in an amount and for a time sufficient to extract essentially all fungi-toxic material in the wood material, separating the agent containing the fungi-toxic material from the wood material, contacting a second quantity of wood material with the separated extraction agent for a time sufficient to extract fungi-toxic material contained in the second quantity of wood material, and separating the extraction agent from the second quantity of wood material.

2. A process according to claim 1 further including the steps of contacting the extraction agent separated from the second quantity of wood material with a third quantity of the wood material for time sufficient to extract fungi-toxic material contained in the wood material.

3. A process in accordance with claim 2 wherein the wood material comprises eastern white cedar.

4. A process in accordance with claim 3 wherein the extraction agent includes an aqueous solution of borax.

5. A process in accordance with claim 2 wherein the wood material includes at least one wood selected from the group consisting of western red cedar, eastern white cedar, yellow cedar, yew, redwood and teak.

6. A process in accordance with claim 1 wherein the first quantity of wood material is contained in a first container and, after separation of the extraction agent from the first quantity, the extraction agent is returned to the first container for contact with the second quantity of wood material.

7. A process in accordance with claim 1 wherein the wood material is in a finely divided state.

8. A process in accordance with claim 1 wherein the second quantity is approximately the same size as the first quantity.

9. A process in accordance with claim 2 wherein the third quantity is approximately the same size as the second quantity.

10. A process in accordance with claim 1 wherein the extraction agent extracts essentially all the fungi-toxic material contained in the second quantity.

11. A process according to claim 2 further including the steps of contacting the extraction agent separated from the third quantity of wood material with a fourth quantity of the wood material for time sufficient to extract fungi-toxic material contained in the wood material.

* * * * *